United States Patent [19]

Scortecci

[11] Patent Number: 4,815,974

[45] Date of Patent: * Mar. 28, 1989

[54] DENTAL IMPLANT FOR THE SECUREMENT OF FIXED DENTAL PROSTHESES, ITS TOOL FOR ITS POSITIONING AND ITS INSERTION PROCESS

[76] Inventor: Gerard Scortecci, 10 rue du Soleil, 06000 Nice, France

[*] Notice: The portion of the term of this patent subsequent to Feb. 2, 2005 has been disclaimed.

[21] Appl. No.: 139,258

[22] Filed: Dec. 29, 1987

Related U.S. Application Data

[62] Division of Ser. No. 810,370, filed as PCT FR85/00064 on Mar. 29, 1985, published as WO85/04321 on Oct. 10, 1985, Pat. No. 4,722,687.

[30] Foreign Application Priority Data

Mar. 29, 1984 [FR] France ................ 84 05129

[51] Int. Cl.⁴ ............................................. A61C 8/00
[52] U.S. Cl. ................................................ 433/173
[58] Field of Search ............... 433/173, 174, 176, 165, 433/166, 225

[56] References Cited

U.S. PATENT DOCUMENTS

| | | | |
|---|---|---|---|
| 2,453,696 | 11/1948 | Brooks | 433/165 |
| 2,857,671 | 10/1958 | Nelson | 433/166 |
| 3,474,537 | 10/1969 | Christensen | 433/174 |
| 3,894,339 | 7/1975 | Manzi | 433/166 |
| 3,905,108 | 9/1975 | Weiss et al. | 433/173 |
| 3,925,892 | 12/1975 | Juillet | 433/176 |
| 3,992,780 | 11/1976 | Herskovits | 433/176 |
| 4,531,915 | 7/1985 | Tatum | 433/173 |

FOREIGN PATENT DOCUMENTS

| | | | |
|---|---|---|---|
| 992085 | 10/1951 | France | 433/166 |
| 1030690 | 6/1953 | France | 433/173 |
| 2302715 | 10/1976 | France | 433/173 |
| 2516784 | 5/1983 | France | 433/173 |
| 392773 | 10/1965 | Switzerland | 433/166 |

Primary Examiner—John J. Wilson
Attorney, Agent, or Firm—Young & Thompson

[57] ABSTRACT

A method is provided for positioning a dental implant, comprising cutting a slot in a jaw bone with a tool comprising a shaft having a flat cutter wheel at one end of relatively large diameter and a plurality of relatively small cutter wheels spaced apart from said relatively large wheel and from each other along said shaft. The cutting is effected by moving the shaft normal to its axis so that the relatively large flat cutter wheel moves into the jaw bone while remaining in a single plane. Upon removing the tool from said slot, an implant is emplaced in the slot comprising a shaft having at one end a relatively large diameter wheel and a plurality of relatively small wheels spaced apart along said shaft from said relatively large wheel and from each other. The relatively large wheel of said implant has a thickness slightly greater than that of said large wheel of said cutter wheel thereby to wedge said implant in the jaw bone, the emplacing of the implant being effected by moving the implant shaft normal to its axis so that the relatively large diameter wheel of the implant moves into the slot while remaining in a single plane.

1 Claim, 3 Drawing Sheets

DENTAL IMPLANT FOR THE SECUREMENT OF FIXED DENTAL PROSTHESES, ITS TOOL FOR ITS POSITIONING AND ITS INSERTION PROCESS

This application is a division, of application Ser. No. 810,370, filed as PCT FR85/00064 on Mar. 29, 1985, published as WO85/04321 on Oct. 10, 1985, now U.S. Pat. No. 4,722,687.

The object of the invention is a dental implant for the fixing of fixed dental prostheses.

The implant is a substructure generally metallic used for supporting a dental prosthesis. It allows to replace the teeth as natural pillars by mechanical pillars placed either into the mandibula or the maxilla.

The essential in the positioning of a dental implant is to obtain an immediate blocking up into the bone. The slightest mobility of the implant inside the bone leads eventually to rejection. Once the implant is set into the bone, a tapped ring or screw is set onto the outside part which is generally a threaded rod. On this tapped ring or screw, the dental prosthesis is fixed with a cement.

The state of the art may be defined by process patent registered on June 12, 1972 under No. 72 21113 and published on Jan. 2, 1974 under No. 2,188,445.

The patent describes an endo-osseous anatomic implant and its insertion process including a grid topped by one or several rods called "false-stump" for the fixing of prostheses, an implant characterized by the fact that the polygon of support of the grid is mainly disposed in a horizontal plane, this grid being shaped so as to be set into the mandibula or the maxilla, according to one or several planes issued from or close to a horizontal plane, so that the grid goes into a trench with one or several approximately horizontal planes made on the vestibular, lingual or palatal side of the maxillar body considered, while the false-stump(s) go(es) at the same time into as many vertical passages cutting the plane(s) of the approximately horizontal trench.

Other implants known as LINKOW's strips can also define the state of the art. These strips are characterized by a strip-shaped hooking part composed of several arched hooking legs ending with feet.

This part as a whole tends to allow the osseous tissue to gradually imbricate between legs and feet so as to fix the implant solidly.

The conception of these implants and the way they are positioned are subject to many drawbacks. The boring of the bone on a vertical plane and a sometimes wide diameter, is necessarily deep to mask the whole height of the implants. Now the bone, very often, does not offer sufficient height and the implants cannot pass round the obstacles such as sinuses, nasal fossae, nerves, the boring having to be effected almost always vertically.

Consequently these types of known implants cannot be adapted to various bony structures. Moreover, these implants, essentially inserted on a vertical plane, present bad characteristics of transmission of the forces imposed on them. They work essentially on edge and have a strong tendency to self-bore under the pressures exerted by mastication.

These implants, inserted on a vertical plane, resist badly the tensile, driving in and side stresses in the four directions.

The positioning of these implants is an awkward operation. It is necessary to form a groove corresponding exactly to the dimensions of LINKOW's strips.

The positioning of an implant described in JUILLET's patent requires a drilling which now can only be achieved in two phases of intervention: a vertical drilling followed by an horizontal drilling or reversely, and this being achieved with tools used separately.

On the other hand, the bone drilling tools are made of either tungsten or steel, or again of another material which is always different from that of the implant itself. There is a risk of polymetallism when the implant is placed into its site of lodging. As a matter of fact, the implant being made of titanium, the titanium will interfere with that tungsten or steel or any material other than titanium.

It is unanimously admitted that, when drilling the bone with a metallic part, metallic particles always remain in the area (osseous territory). So, both the tool and the implant must be manufactured with the same metal to avoid a bi-metallism generating tissue lesion.

The invention tends to solve all these drawbacks. Especially, the invention tends to ensure a faultless primary fixation owing to the preciseness with which the lodging of the implant is cut into the bone.

The implant according to the invention is characterized by the fact that the tool necessary to cut the lodging can stay in place and be used as a dental implant. The compulsory consequence is that the implant corresponds exactly to the lodging formed by the tool.

This implant has a double function:

(1) It is used as an artificial root in replacement of the missing natural dental pillars. It is its main and final function.

(2) At the same time, it can be its own boring tool. Its indented structure (on the wheel) and milled, on the axis, allows this implant, once it is placed on a rotating instrument (owing to its smooth "junction" tip), to be used as a drilling tool of the implant lodging (maxilla) which will receive it.

The smooth tip prolonging the milled part and the possible threading was specially elaborated to adapt directly on a high speed turbine or micro-motor. In case of need a supplementary notch can also been provided on the tips of the shafts to receive the blocking clamps of drills at slow and medium speed and hand tools.

The characteristic of this tool-implant is to achieve in one single phase a micro-osteotomy by drilling, simultaneously in the horizontal and vertical planes, in other words in two perpendicular planes.

Another advantage of the tool-implant: this drill-tool rotates (once clamped onto the turbine, the micro-motor or the drill or the hand tool) around its axis.

When placing it laterally against the bony wall, the practitionner, in a straight-line translation movement, allows the intra and trans-osseous penetration in a plane parallel to that of the indented wheel, for the base or wheel. At the same time, he achieves a simultaneous penetration of the rod in a plane perpendicular to the base or wheel.

According to another conception, the tool can be recovered and an implant corresponding to the formed lodging can be positioned. In this case, the implant to the positionned has characteristics slightly different from the tool in order to be "forced" into the said lodging. Consequently, the implant profile is identical to that of the tool but some parts are not sharpened, others are thicker to avoid any mobility of the implant in its lodging. The base of the wheel has a smooth edge instead of being indented. The rod can be either smooth or threaded.

The tool implant according to the invention consists of a rod with at one end, a smooth part used as junction tip prolonged by a threaded part allowing to fix a tapped ring or screw. The junction tip of the tool implant may have an adaptation clamp for the drills and hand tools. At the other end of the said rod, at least one indented wheel is placed: the said wheel is perpendicular to the longitudinal axis of the rod to allow horizontal drilling while the vertical drilling is achieved by a part of the rod the base of which is milled from at least one of the indented wheels.

The milled part of the rod which is set at the base of the said rod, from the indented wheel, is composed of circular furrows or grooves the edges of which are sharpened. So this part can cut vertically when the rod is operated by a rotating instrument.

The grooving was elaborated in a special way so as to obtain a maximum cutting action for a minimum overheating and trauma where the osseous tissue is concerned. A notching in the horizontal direction allows the chips to be cleared out, while lowering the overheating of the osseous tissue.

The indented wheel has sharpened teeth on its periphery, it can cut horizontally when the said rod is operated by a rotating instrument.

The indented wheel may have holes which allow reducing the weight of the material of the tool-implant, without reducing the mechanical qualitites.

The insertion process of such a tool-implant consists in helving the turbine onto the junction tip of the said tool-implant, as soon as it rotates: a microosteosection by drilling can be achieved in one phase, at the same time in a horizontal and vertical plane, that is to say in two perpendicular planes. The number of wheels determines the number of horizontal planes.

The tool-implant is placed in the lodging formed by the slot corresponding to the profile projected laterally of the tool or the tool-implant. The toolimplant or the independent implant is inserted laternally into the said slots preferrably on the vestibular side so that only the end of the rod opposite to that of the wheel protrudes from the bone edge. The rod is cut at required height to receive the screw or tapped ring. There is not adjusting needed since both tool and implant form one part. Before its final biological blocking by regeneration of the bone around the implant and specially around the milled part, the said implant is perfectly stable owing to the quality of the technical characteristics of its lodging.

According to another conception, the implant is independent from the tool.

The tool according to the invention is characterized by the fact that it presents all the technical characteristics of the tool-implant described here above.

The independent implant properly speaking presents all the technical characteristics of the tool, with the essential technical differences hereunder:

In the milled part, the circular furrows or grooves are less sharpened than those of the tool, so the edges are less sharp. In some shapes, they do not exist. Consequently the body is either smooth or threaded.

The circumference of the wheel perpendicular to the longitudinal axis of the tool is smooth, so, it presents no cogs. The smooth wheel is slightly thicker than the indented wheel of the tool so as to be "forced" into the lodging created by the indented wheel of the tool.

According to a preferred conception, the rod of the tool and implant and/or tool implant has only one wheel. According to another conception, the wheel perpendicular to the longitudinal axis of the rod is removable and thus can be fixed to the end of the said rod when necessary.

According to another conception, two parallel wheels can be mounted onto the same rod. This conception is not represented in the drawings.

The attached drawings are given merely as an indication and are not restrictive: they will make the understanding of the inention easy. The show some preferred conceptions, according to the invention.

Figure 1:
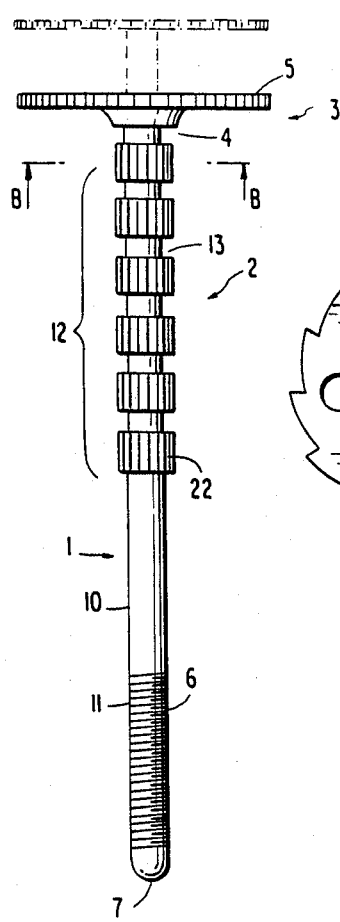
FIG. 1 shows a side view of the tool of the tool-implant.
Figure 2:
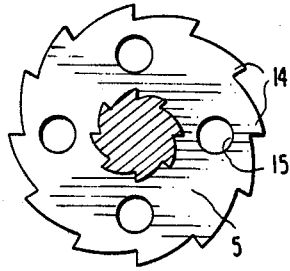
FIG. 2 is a section view of the tool of the tool-implant according to axis BB represented in FIG. 1.

The tool-implant 1 according to the invention is composed of a part 2 used as a vertical drill and another part 3 perpendicular to the longitudinal axis and used as drill-wheel 5. Part 2 is equipped at its base 4 with an indented wheel 5 perpendicular to the longitudinal axis and at its other end 7 with fixing device 6 which allows the fixing of the tapped ring or screw S on which the dental prosthesis 9 and/or a smooth part used as junction tip 11 are positioned.

The tool-implant 1 is composed of only one part, consisting of a rod 10 having a junction tip 11 which helves into the spindle of turbine 23: this junction tip 11 may have at its end 7, a fixing device 6 which allows the positioned of a tapped ring or screw S. The said fixing device 6 can be for instance a threading of this end 7 of the tool-implant 1. The profile of the tapped ring or screw is special, it consists of two inverted truncated cones, a and b, a large and a small one.

"a" is the large truncated cone: it is intended to receive the tooth or the prosthetic superstructure.

"b" is the small truncated cone: it is contiguous to the gum and is shaped so as to allow the gum tissue to take the exact shape of its circumference. This limits the risks of irritation and retention of the bacterial plaque and food remains. The inverted truncated cone b suppresses any overhanging and thus the blocking of the substances at this level. This shape takes the most up-to-date periodontal concepts into account.

The other end 2 of the tool-implant 1 includes a milled part 12 ending with an indented wheel 5 perpendicular to the longitudinal axis.

The milled part 12 presents circular furrows or grooves 13 the edges of which are sharpened and form mills 22 grooved in the direction of the longitudinal axis of the rod, so as to obtain a maximum cutting action with a minimum over-heating and osseous trauma. A notching in the horizontal direction allows the chips to be cleared out while lowering the over-heating of the osseous tissue.

Wheel 5 has sharpened teeth 14 on its periphery.

Wheel 5 my have for instance four holes 15 which allow reducing the weight of the material of the tool-implant and this, without reducing the mechanical qualitites. The osseous tissue grows through the implant through these holes and ensures part of the final biological blocking: the imprisonment of the base plus rod set by the bone ensures the rest of the blocking.

According to another conception, the implant is independent from the tool.

(1) The tool has all the technical characteristics described above for the tool-implant (see FIG. 1).

Figure 3:
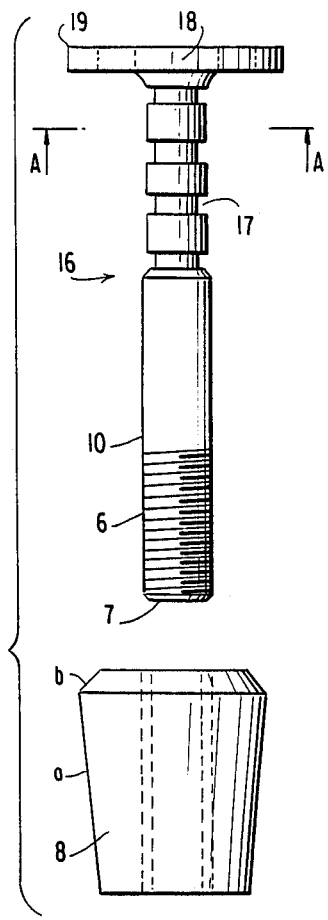
FIG. 3 is a side view of the implant independent from the tool.
Figure 4:
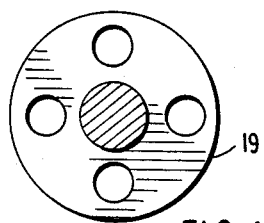
FIG. 4 is a section view according to axis AA of the implant independent from the tool, as shown in FIG. 3.
Figure 5:
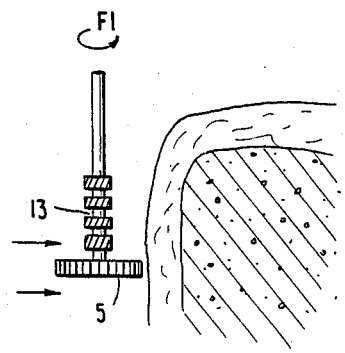
FIG. 5 is a schematic view of a rotating tool cutting an implant lodging into the maxilla.
Figure 6:
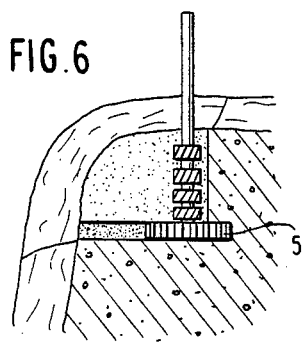
FIG. 6 is a schematic view of a tool which, by rotating according to Arrow F1, has bored the lodging or site for the implant into the maxilla.
Figure 7:
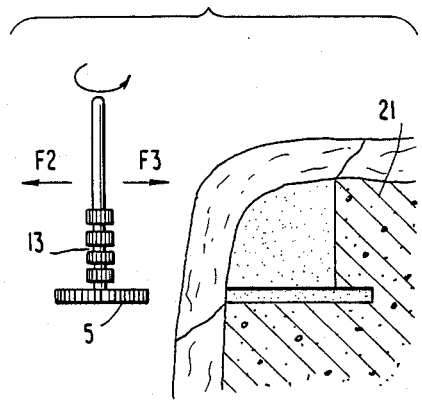
FIG. 7 shows that the tool-implant or the tool can go laterally into and out of the lodging of the implant according to Arrows F2, F3. The implant has just to be inserted laterally into the slot created by the profile of the tool-implant or the tool.
Figure 8:
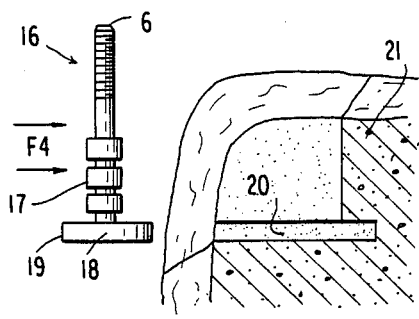
FIG. 8 represents an independent implant about to be forced into its lodging according to Arrow F4. It should be noted that the furrows or grooves are not sharpened, that the smooth wheel is thicker than the indented wheel of the tool, which ensures a perfect mobility of the implant in its lodging or site.

(2) The implant properly speaking 16 has all the technical characteristics described above for the tool-implant 1 with the essential technical differences hereunder (see FIG. 3):

the milled part 12 no longer has a vertical cutting action, so the edges of the furrows or grooves 17 are less sharp than for mills 22. This part no longer has a cutting action, but only a retaining action. Thus circular furrows 17 are less sharpened, the edges are less sharp.

the smooth wheel 18, perpendicular to the axis of the rod does not have any teeth on its periphery, moreover, it is thicker at 19 than the indented wheel 5 of tool 1, so as to force-fit the implant lodging 20 created by the indented wheel 5 of tool 1.

Figure 9:
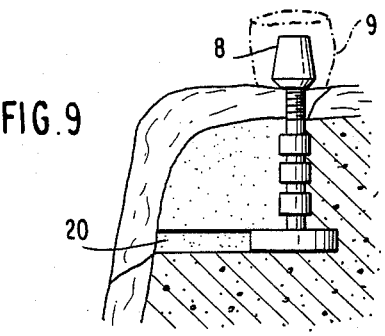
FIG. 9 is a schematic view of an implant independent from the tool, positioned in its implant lodging: the end of the implant is equipped with an attaching device, as for instance a threading which allows the fixing of the body; on that tapped ring or screw the dental prosthesis will be cemented.
Figure 10:
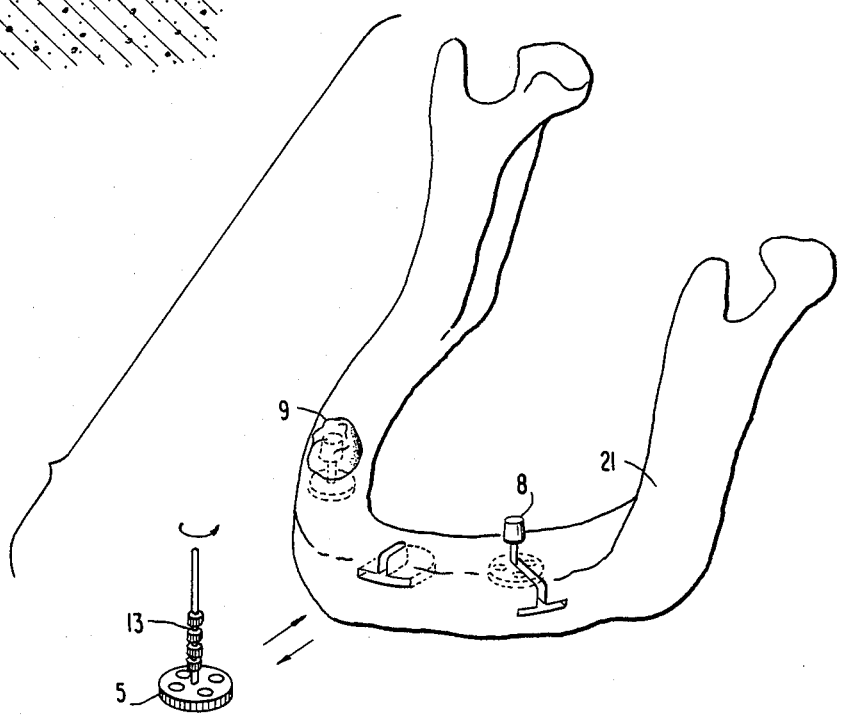
FIG. 10 is a perspective view of a lower jaw showing positioned implants, with their tapped ring or screw ready to receive the prosthesis, a tool in operation, a lodging or site for implant.
Figure 11:
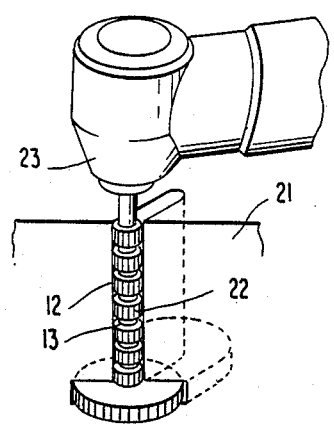
FIGS. 11, 12, 13 show the operating of the tool implant boring into the bone a slot corresponding to its profile.
Figure 12:
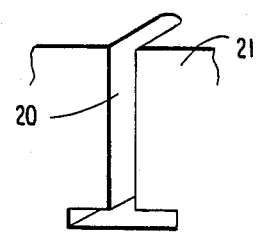
Figure 13:
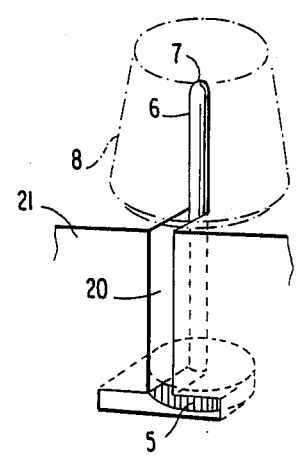
Figure 14:
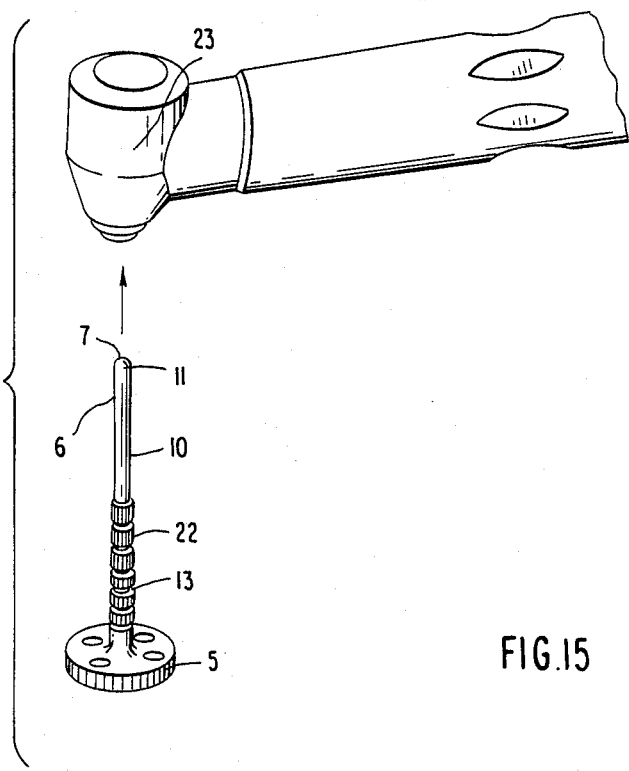
FIG. 14 shows how the junction tip allows the fixing of the tool or the tool-implant into the spindle of the turbine.
Figure 15:
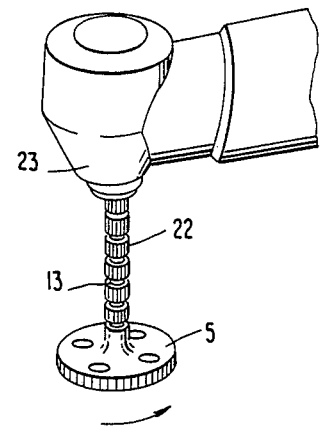
FIG. 15 shows a turbine in operation with air and water jets for cooling.

FIG. 11 shows the cutting action of the tool or tool implant into the bone to achieve a slot corresponding to the implant lodging or site 20. This lodging 20 corresponds to the profile projected laterally of the said tool or tool-implant to be inserted laterally into the said slot. Only the end 7 of rod 10 opposite to indented wheel 5 or the smooth wheel 18 perpendicular to the longitudinal axis of the said rod 10 protrudes from the edge of bone 21. FIG. 9 shows implant 1 or tool-implant 16 positioned, equipped with the prosthetic tooth 9 after rod 10 has been cut to the required height and has received the corresponding threaded screw 8.

I claim:

1. A method of positioning a dental implant, comprising cutting a slot in a jaw bone with a tool comprising a shaft having a flat cutter wheel at one end of relatively large diameter and a plurality of relatively small cutter wheels spaced apart from said relatively large wheel and from each other along said shaft, said cutting being effected by moving the shaft normal to its axis so that the relatively large flat cutter wheel moves into the jaw bone while remaining in a single plane, removing said tool from said slot, and emplacing in the slot an implant comprising a shaft having at one end a relatively large diameter wheel and a plurality of relatively small wheels spaced apart along said shaft from said relatively large wheel and from each other, said relatively large wheel of said implant having a thickness slightly greater than that of said large wheel of said cutter wheel thereby to wedge said implant in the jaw bone, the emplacing of the implant being effected by moving the implant shaft normal to its axis so that the relatively large diameter wheel of the implant moves into the slot while remaining in a single plane.

* * * * *